(12) United States Patent
Huhn

(10) Patent No.: US 7,501,277 B2
(45) Date of Patent: Mar. 10, 2009

(54) CELL TREATMENT CHAMBER

(75) Inventor: Rudiger Huhn, Lubek (DE)

(73) Assignee: Eppendorg AG, Hamburg (DE)

( * ) Notice: Subject to any disclaimer, the term of this patent is extended or adjusted under 35 U.S.C. 154(b) by 659 days.

(21) Appl. No.: 10/982,630

(22) Filed: Nov. 4, 2004

(65) Prior Publication Data

US 2005/0064580 A1 Mar. 24, 2005

(30) Foreign Application Priority Data

Nov. 6, 2003 (DE) ................................ 103 51 833

(51) Int. Cl.
*C12M 1/42* (2006.01)

(52) U.S. Cl. .................... 435/285.2; 435/450; 435/461; 435/470

(58) Field of Classification Search ....................... None
See application file for complete search history.

(56) References Cited

U.S. PATENT DOCUMENTS

| 4,764,473 | A | * | 8/1988 | Matschke et al. | ........ | 435/285.2 |
| 4,921,738 | A | | 5/1990 | Cassidy | .................... | 428/34.6 |
| 6,229,209 | B1 | | 5/2001 | Nakamura et al. | .......... | 257/737 |
| 2002/0160437 | A1 | * | 10/2002 | Meyer | ......................... | 435/15 |

FOREIGN PATENT DOCUMENTS

| DE | 3317415 | 11/1984 |
| DE | 10127247 | 12/2002 |
| EP | 1245669 | 10/2002 |

* cited by examiner

*Primary Examiner*—James S Ketter
(74) *Attorney, Agent, or Firm*—Vidas, Arrett & Steinkraus, P.A.

(57) ABSTRACT

Chamber for treating cells contained in a suspension in the electrical field with a beaker made from electrically non-conductive material, into which an elongate core made from electrically non-conductive material is at least partially inserted axially through an opening, between the beaker and the core a gap being present to receive the suspension; at least two electrodes made from electrically conductive material arranged on the outer face of the core facing the gap, between which an electrical field can be created to treat cells in a suspension contained in the gap by applying a voltage; the thermal expansion coefficient of the material of the electrodes and of the material of the core being matched with one another such that the electrodes do not substantially alter their position relative to the core in the temperature range from ambient temperature to temperatures reached during auto-claving and/or sterilising.

20 Claims, 3 Drawing Sheets

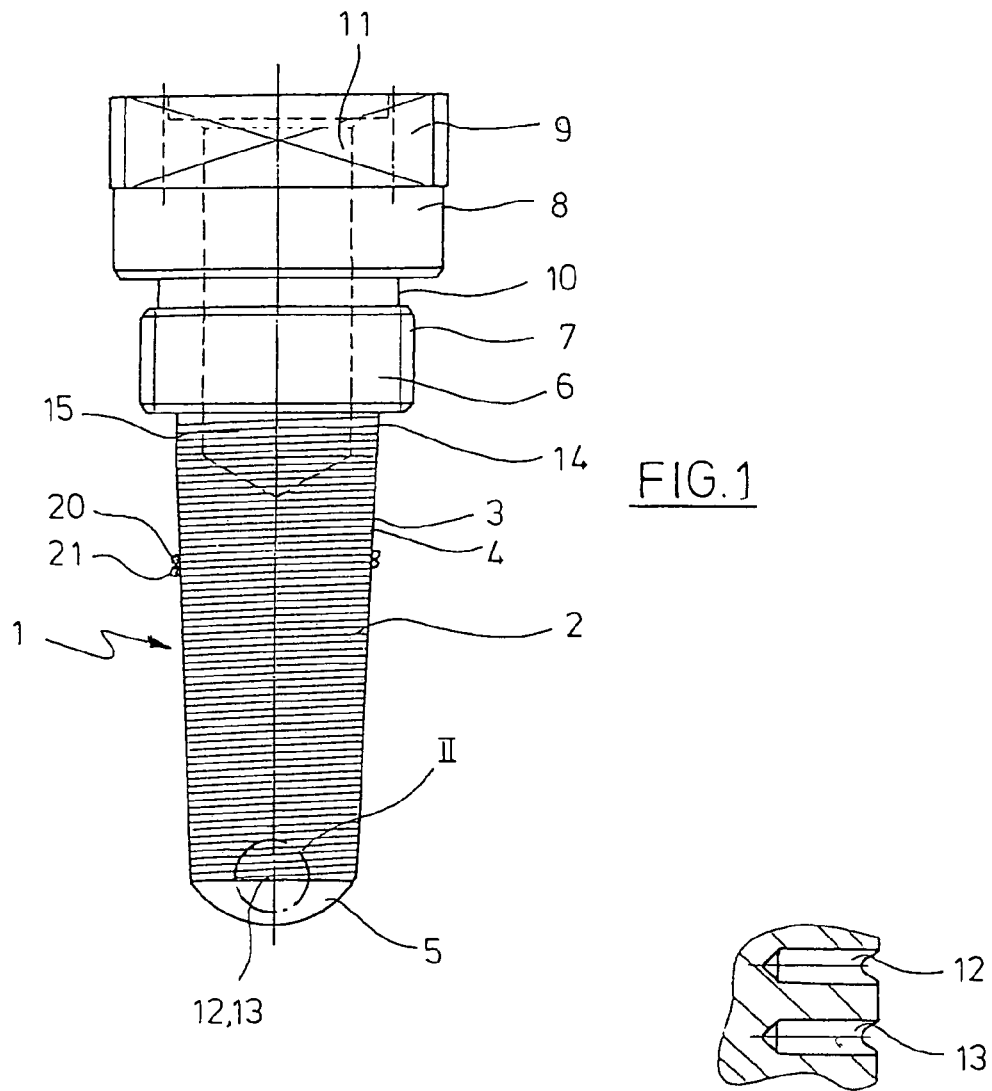
FIG.1
FIG.2
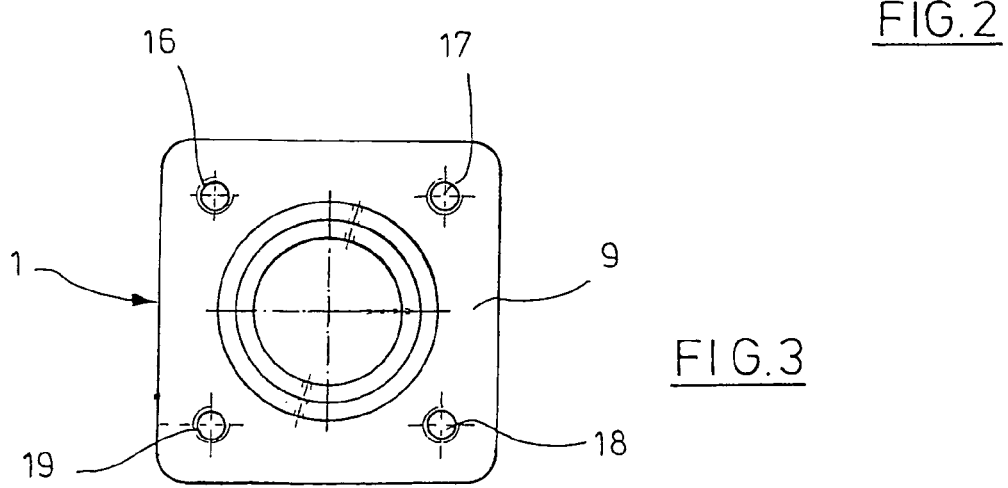
FIG.3

CELL TREATMENT CHAMBER

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to a chamber for treating cells contained within a suspension in the electrical field.

The chamber according to the invention serves, for example, the electrofusion of cells. In electrofusion at least two cells are fused in an electrical field which is created between two electrodes. The electrofusion can, for example, take place in three steps. In a first step (pre-alignment) the cells are aligned by applying a high frequency AC voltage and brought into contact with one another. In a second step (pulse) the cell membranes are broken down by means of a short strong current pulse. In a third step (post-alignment) the broken-down cells are fused together by further application of a high frequency AC voltage or held, in order to allow automatic fusion.

Cell fusion chambers are known in which two thin platinum wires which form the electrodes are wound parallel in a pair of helically-shaped flutes on a conical body made from non-conductive plastics. Furthermore, the cell fusion chambers have a conical beaker into which the plastics body can be screwed. Protruding over the upper face of the beaker, the plastics body has a head on which a plug is mounted which is connected to the electrodes. The high frequency AC voltage can be supplied via the plug. The manufacture of cell fusion chambers is costly and expensive, so that multiple use of the cell fusion chambers is economically desirable. For this, the cell fusion chambers have to be cleaned mechanically and with cleaning agents between different uses which is expensive. The known cell fusion chambers are not autoclavable or sterilisable, as they generally are no longer functional after a corresponding treatment.

From this the object of the invention is to create a cell fusion chamber which is autoclavable and/or sterilisable.

BRIEF SUMMARY OF THE INVENTION

The chamber according to the invention for treating cells contained in a suspension in the electrical field has a beaker made from electrically non-conductive material, into which an elongate core made from electrically non-conductive material is at least partially inserted axially through an aperture, between the beaker and the core a gap being present to receive the suspension; at least two electrodes made from electrically conductive material arranged on the outer face of the core facing the gap, between which an electrical field can be produced by applying a voltage to treat cells in a suspension contained in the gap; the thermal expansion coefficient of the material of the electrodes and the material of the core being so similar to one another, that the electrodes substantially retain their position relative to the core in the temperature range from ambient temperature to the temperatures reached when autoclaving and/or sterilising.

In the context of the invention it is recognised that the lack of autoclavability and sterilisability of conventional cell fusion chambers is due to the fact that the platinum wires alter their position on the core as a result of heating. It is recognised that this is due to the great difference in thermal expansion of the platinum wires and the plastics material of the core. The thermal expansion coefficient (Note: strictly speaking the thermal coefficient of linear expansion) of the core material which is higher by at least to the power of ten leads to the fact that with a rise in temperature the core expands more than the wires. In the process, the wire is plastically deformingly stretched. When the temperature is lowered the wires then slip relative to the core, so that it leads to short circuits between the different windings. According to the invention this is avoided by matching the thermal expansion coefficients of the material of the electrodes and the material of the core. The matching is carried out to such an extent that the electrodes substantially retain their position relative to the core in the entire temperature range from ambient temperature (approximately −21 to +35° C.) to the typical temperatures for autoclaving and/or sterilising (approximately +120 to +180° C.). The electrodes substantially retain their position relative to the core, whilst they are not displaced to such an extent that a short circuit occurs.

According to an embodiment the thermal expansion coefficients of the material of the electrodes and the material of the core are matched with one another, such that the electrodes do not substantially alter their position relative to the core up to temperatures reached during steam sterilisation and/or radiation sterilisation (approximately +120 to +140° C.).

According to an embodiment the core is cylindrical or conical and/or the beaker cylindrical and/or conical externally and/or internally. As a result the manufacture of electrodes by the winding of wires is in particular facilitated. With complementary shapes of cores and beakers the gap has a consistent depth which is again advantageous for the consistent treatment of the cells in the suspension.

According to an embodiment the electrodes are wires which are wound onto the core as a multithread in the shape of a helix or a ramp. The helically-shaped path is, for example, present with a cylindrical or conical core and the ramp-shaped path, for example, with a polyhedral core.

According to an embodiment the core has a plurality of helically-shaped or ramp-shaped extending flutes or grooves on the outer face, in which the wires are guided. As a result the wires are also prevented from slipping which could occur as a result of slight remaining differences in the thermal expansion coefficient or due to the mechanical effect on the wires.

According to an embodiment the wires comprise offset ends which are inserted into radial bores of the core. As a result the wires are securely fixed to the core. Furthermore, the wires can be connected through the radial bores to a high frequency voltage generator. According to a further embodiment the offset wire ends are fixed into the radial bores by means of a non-cytotoxic adhesive. It is understood that the adhesive is permanent in the temperature range in which the chamber can be used.

According to an embodiment the electrodes are conductor paths arranged on the core. The conductor paths can, for example, be produced by surface coating the core with an electrically conductive material, partially covering the regions provided as conductor paths and chemically separating the uncovered regions of the coating. According to an embodiment a bonding agent is arranged between the core and the conductor paths which increases the adhesion of the material of the conductor paths on the material of the core.

The conductor paths also extend, for example, as a multi-thread in the shape of a helix or parallel to the longitudinal axis of the core. According to an embodiment the conductor paths have an interdigital structure, i.e. comb-like interlocking regions.

The core can be fixed in different ways relative to the beaker. The fixing preferably takes place directly onto the beaker. To this end, according to an embodiment the core comprises a male thread over the electrodes and the beaker comprises a female thread below an aperture for screwing in the male thread. The core can then simply be screwed into the beaker at the end of an axial insertion movement. According to an embodiment the core comprises a head above the electrodes. The head can be used to handle the core, whereby contamination of the electrodes can be avoided. The head is preferably formed on the periphery in a manner which facilitates the screwing into the beaker.

According to an embodiment the core has a blind hole emerging from the upper face, into which the electrodes are guided. The electrodes can be contacted externally through the blind hole, in order to apply the high frequency voltage.

According to a further embodiment which facilitates the contacting, the electrodes are connected to a plug on the upper face of the core.

According to an embodiment the electrodes are made from platinum. As an inert material, platinum is particularly suitable for the treatment of cells in a suspension. The electrodes designed both as wires and as conductor paths can be produced from platinum. Platinum has a thermal expansion coefficient of $9.0 \times 10^{-6}$ 1/K.

According to an embodiment the core is made from glass ceramic. Thus, for example, glass ceramic with a thermal expansion coefficient of $9.3 \times 10^{-6}$ 1/K is available. Particularly advantageous is the combination of electrodes made from platinum with a core made from glass ceramic, as it connects the inert material to the electrodes with a complete matching of the thermal expansion coefficient. With this combination of materials it is achieved that the electrodes substantially retain their position relative to the core in the entire temperature range from ambient temperature to temperatures during autoclaving and/or sterilising. Platinum and glass ceramic can moreover be sterilised by radiation.

According to an embodiment the core is machined from machinable glass ceramic or injection moulded from glass ceramic. A suitable machinable material is proposed with the product name MACOR® from Corning. During the ceramic injection moulding process, ceramic in the powder state is mixed with polymer matrix and processed to granules. An injection moulding machine is loaded with this which discharges a green compact. This is sintered in order to expel substantially the organic phase and to densify the ceramic article.

In the known chambers the core and beaker consist of PMMA and the plug of PTFE. These materials have the additional disadvantage of not being sterilisable by radiation. According to an embodiment the beaker consists of PC and/or the plug of PEEK. These materials can be sterilised by radiation.

BRIEF DESCRIPTION OF THE DRAWINGS

The invention will be described in more detail hereinafter with reference to the accompanying drawings of embodiments, in which:

FIG. 1 is a side view of a core;
FIG. 2 is an enlarged detail II of FIG. 1;
FIG. 3 is a top view of the core.

DETAILED DESCRIPTION OF THE INVENTION

Figure 4:
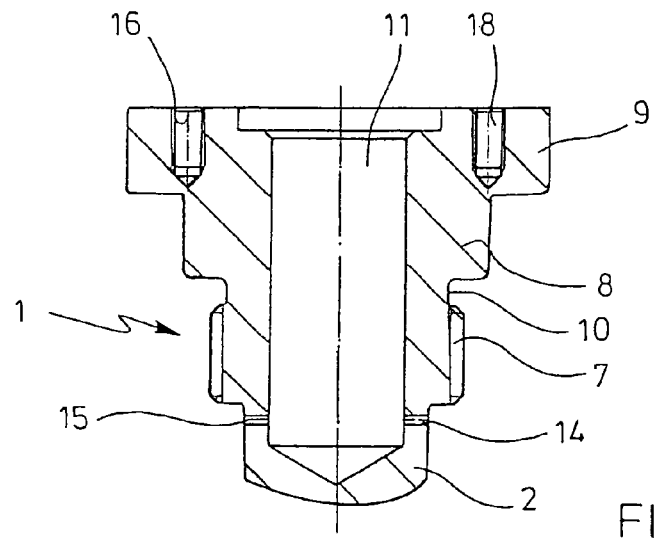
FIG. 4 is an upper section of the core in longitudinal section.

While this invention may be embodied in many different forms, there are described in detail herein a specific preferred embodiment of the invention. This description is an exemplification of the principles of the invention and is not intended to limit the invention to the particular embodiment illustrated The position of the elements of the chamber is referred to as 'above' and 'below' in a typical application, in which the beaker is positioned with the base on a substrate and with the opening arranged vertically over the base. Accordingly, the core which is aligned coaxially to the beaker is arranged with the head and the plug vertically over the opening of the beaker.

According to FIGS. 1 to 4, a core 1 has a slightly conical carrying portion 2, on which two parallel flutes 3, 4 extend in a helical form. At the end of the carrying portion 2 with the smaller diameter, the core 1 comprises a spherical lower end portion 5. At the end of the carrying portion 2 with the larger diameter, the core 1 has a threaded portion 6, which has a markedly larger diameter than the adjacent end of the portion 2 and a male thread 7.

The core 1 comprises a head 8 at the top which is shaped in the upper region as a rectangular plate 9. The head 8 and threaded portion 7 are separated from one another by an indentation 10.

The core 1 further comprises a blind hole 11 emerging from the upper end, which extends in the longitudinal direction of the core 1 as far as the region of the carrying portion 2. Additionally the carrying portion 2 has two radial bores 12, 13 arranged over one another at the lower end, which are designed as blind holes. At the upper end it has two diametrically opposed radial bores 14, 15 which open out into the blind hole 11. In the plate 9 the core 1 has four short axial threaded holes 16, 17, 18, 19.

Electrodes in the form of wires made from platinum 20, 21 are wound parallel onto the carrying portion 2 and guided with their ends into the radial bores 12, 13 and 14, 15. They are fixed in the radial bores by means of a suitable non-cytotoxic adhesive. In the drawings only two parallel windings of the platinum wires 20, 21 are shown. The platinum wires 20, 21, however, actually extend substantially over the entire length of the flutes 3, 4.

A plug—not shown—is arranged on the head 8 of the core 1 and screwed there with the threaded holes 16, 17, 18, 19 of the plate 9. The plug is electrically connected to the upper ends of the wires 20, 21.

The electrodes 20, 21 therefore consist of platinum wire. The core 1 is machined from MACOR® glass ceramic from Corning. The plug is produced from PEEK.

Figure 5:
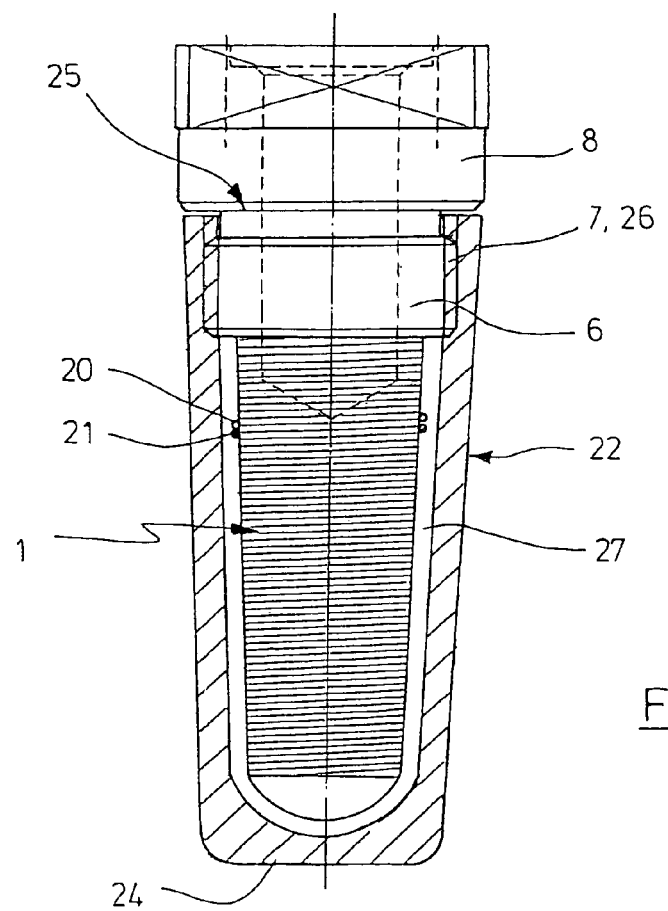
FIG. 5 is a longitudinal section of the chamber.

According to FIG. 5 an associated beaker 22 has an internally and externally conical sleeve 23, of which the cone angle corresponds to that of the carrying portion 2 of the core 1. Furthermore, the beaker 22 has a base 24 with a flat lower face and an opening 25 opposite this at the upper end. Below the opening 25 a female thread 26 is present. The beaker 22 consists of PC.

For the treatment of cells contained in a suspension the core 1 and the beaker 22 are first autoclaved or steam- or radiation sterilised. Due to the materials used this is possible without affecting the functionability of the chamber 1, 22.

Then the suspension is filled into the beaker 22 and finally the core 1 axially inserted and screwed in. The suspension then fills the gap 27 between the core 1 and the beaker 22.

Finally a high frequency voltage generator is connected to the plug and the treatment of the cells carried out.

Figure 6:
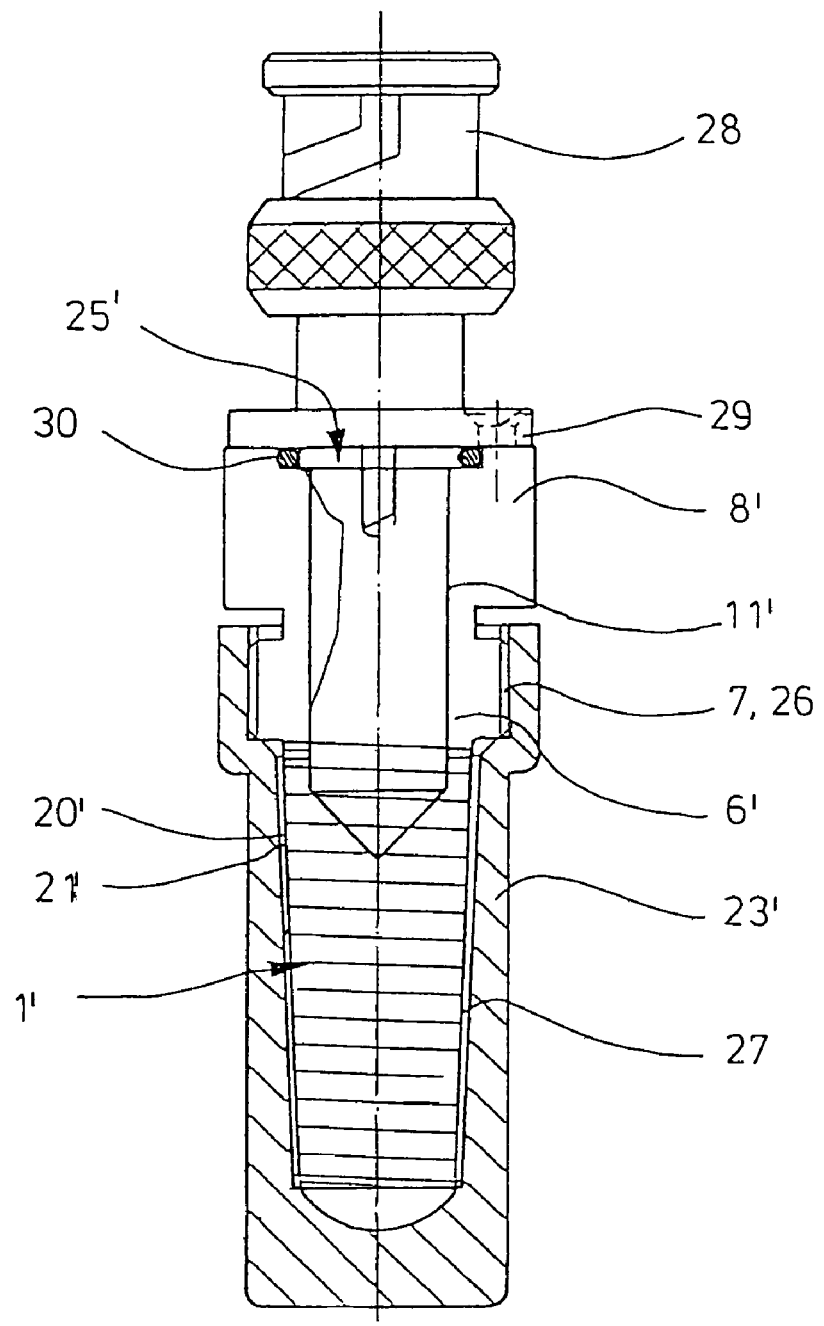
FIG. 6 is a longitudinal section of a further chamber.

In the embodiment of FIG. 6 the features substantially corresponding to the embodiment of FIGS. 1 to 5, are designated by the same reference numerals, which are however provided with an upstroke.

In the chamber of FIG. 6 the core 1' comprises a plug 28 which is fixed at the top on the head 8'. To this end the plug 28 has a fastening plate 29 which is screwed to the upper face of the head 8', a sealing ring 30 being located therebetween. The platinum wires 20', 21' are connected within the blind hole 11' to contacts of the plug 28.

The beaker 23' is internally conical corresponding to the cone of the core 1'. Externally the beaker 23' is cylindrical.

Additionally, the explanations apply to the embodiment of FIGS. 1 to 5.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. Chamber for treating cells contained in a suspension in the electrical field with a beaker (22) made from electrically non-conductive material, into which an elongate core (1) made from electrically non-conductive material is at least partially inserted axially through an opening (25), between the beaker (22) and the core (1) a gap (27) being present to receive the suspension; at least two electrodes (20, 21) made from electrically conductive material arranged on the outer face of the core (1) facing the gap (27), between which an electrical field can be created to treat cells in a suspension contained in the gap (27) by applying a voltage; the thermal expansion coefficient of the material of the electrodes (20, 21) and of the material of the core (1) being matched with one another, such that the electrodes (20, 21) do not substantially alter their position relative to the core in the temperature range from ambient temperature up to temperatures reached during autoclaving and/or sterilising.

2. Chamber according to claim 1, in which the thermal expansion coefficient of the material of the electrodes (20, 21) and the material of the core (1) are matched with one another such that the electrodes (20, 21) do not substantially alter their position relative to the core (1) up to temperatures reached during steam- and/or radiation sterilisation.

3. Chamber according to claim 1, in which the core (1) is cylindrical or conical and/or the beaker (22) is cylindrical and/or conical externally and/or internally.

4. Chamber according to claim 1, in which the electrodes (20, 21) are wires, which are wound as a helical- or ramp-shaped multi-thread on the core (1).

5. Chamber according to claim 4, in which the core (1) has a plurality of helically or ramp-shaped extending flutes (3, 4) or grooves on the outer face in which the wires (20, 21) are guided.

6. Chamber according to claim 4, in which the wires (20, 21) comprise offset ends which are inserted into radial bores (12, 13, 14, 15) of the core (1).

7. Chamber according to claim 6, in which the offset ends are fixed by means of a non-cytotoxic adhesive in the radial bores (12, 13, 14, 15).

8. Chamber according to claim 1, in which the electrodes (20, 21) are conductor paths arranged on the core (1).

9. Chamber according to claim 8, in which a bonding agent is arranged between the core (1) and the conductor paths.

10. Chamber according to claim 1, in which the conductor paths comprise an interdigital structure.

11. Chamber according to claim 1, in which the core (1) comprises a male thread (7) above the electrodes (20, 21) and the beaker (22) comprises a female thread (26) below an opening (25) for screwing in the male thread (7).

12. Chamber according to claim 1, in which the core (1) comprises a head (8) above the electrodes (20, 21).

13. Chamber according to claim 1, which comprise an axial blind hole (11) which is extended from the upper end of the core (1) as far as approximately level with the electrodes (20, 21).

14. Chamber according to claim 1, in which the electrodes (20, 21) are connected to a plug (28) on the upper face of the core (1).

15. Chamber according to claim 1, in which the electrodes (20, 21) are made from platinum.

16. Chamber according to claim 1, in which the core (1) is made from glass ceramic.

17. Chamber according to claim 1 with a core (1) machined from machinable glass ceramic or injection moulded from glass ceramic.

18. Chamber for treating cells contained in a suspension in the electrical field with a beaker (22) made from electrically non-conductive material, into which an alongate core (1) made from electrically non-conductive material is at least partially inserted axially through an opening (25), between the beaker (22) and the core (1) a gap (27), being present to receive the suspension; at least two electrodes (20,21) made from electrically conductive material arranged on the outer face of the core (1) facing the gap (27), between which an electical field can be created to treat cells in suspension contained in the gap (27) by applying a voltage; the thermal expansion coefficient of the material of the electrodes (20,21) and of the material of the core (1) being matched with one another, such that the electrodes (20,21) do not substantially alter their position relative to the core in the temperature range from ambient temerature up to temperatures reached during autoclaving and/or sterilising wherein the beaker (22) is made from PC.

19. Chamber according to claim 14 with a plug (28) made from PEEK.

20. Chamber for treating cells contained in a suspension in the electrical field with a beaker (22) made from electrically non-conductive material, into which an elongate core (1) made from electrically non-conductive material is at least partially inserted axially through an opening (25), between the beaker (22) and the core (1) a gap (27) being present to receive the suspension; at least two electrodes (20, 21) made from electrically conductive material arranged on the outer face of the core (1) facing the gap (27), between which an electrical field can be created to treat cells in a suspension contained in the gap (27) by applying a voltage; the thermal expansion coefficient of the material of the electrodes (20, 21) and of the material of the core (1) being matched with one another, such that the electrodes (20, 21) do not substantially alter their position relative to the core in the temperature range from ambient temperature up to temperatures reached during autoclaving and/or sterilising, wherein the core (1) is machined from machinable glass ceramic or injection moulded from glass ceramic.

* * * * *